US006346264B1

(12) United States Patent
White

(10) Patent No.: US 6,346,264 B1
(45) Date of Patent: Feb. 12, 2002

(54) SUPPLEMENT FOR RESTORING GROWTH HORMONE LEVELS

(75) Inventor: Philip White, Kelowna (CA)

(73) Assignee: International Health Products and Services Ltd., Bridgetown (BB)

( * ) Notice: Subject to any disclaimer, the term of this patent is extended or adjusted under 35 U.S.C. 154(b) by 0 days.

(21) Appl. No.: 09/560,698

(22) Filed: Apr. 27, 2000

Related U.S. Application Data

(60) Provisional application No. 60/131,117, filed on Apr. 27, 1999.

(51) Int. Cl.$^7$ ............................................. A61K 47/00
(52) U.S. Cl. ........................ 424/439; 424/400; 424/484; 424/489
(58) Field of Search ........................... 424/141.1, 184.1, 424/195.1, 449, 450, 451, 464, 489, 85.4; 435/6, 69.7, 325; 530/324, 328, 329; 514/1, 11, 12, 16, 565, 573, 169

(56) References Cited

U.S. PATENT DOCUMENTS

| | | | | |
|---|---|---|---|---|
| 4,839,344 A | * | 6/1989 | Bowers et al. | 514/16 |
| 4,880,777 A | * | 11/1989 | Momany | 514/12 |
| 5,051,249 A | | 9/1991 | Metcoff | |
| 5,179,080 A | * | 1/1993 | Rothkopf | 514/12 |
| 5,374,651 A | | 12/1994 | Kilbourn | |
| 5,504,072 A | | 4/1996 | Schmidl et al. | |
| 5,576,351 A | * | 11/1996 | Yoshimura et al. | 514/565 |
| 5,607,691 A | * | 3/1997 | Hale et al. | 424/449 |
| 5,667,806 A | * | 9/1997 | Kantor | 424/484 |
| 5,691,325 A | | 11/1997 | Sandyk | |
| 5,719,119 A | | 2/1998 | Veech | |
| 5,766,633 A | * | 6/1998 | Milstein et al. | 424/489 |
| 5,935,601 A | * | 8/1999 | Leone-Bay et al. | 424/489 |
| 5,976,569 A | * | 11/1999 | Milstein | 424/451 |

FOREIGN PATENT DOCUMENTS

| | | |
|---|---|---|
| EP | 0182356 | 5/1986 |
| EP | 0347890 | 12/1989 |
| EP | 0 399 341 A1 | 11/1990 |
| EP | 0 418 593 A | 3/1991 |
| EP | 0 656 178 A2 | 6/1995 |
| GB | 913790 | 12/1962 |
| GB | 1 339 522 | 3/1972 |
| WO | WO 91/09524 A | 7/1991 |
| WO | WO 94/14458 A1 | 7/1994 |

OTHER PUBLICATIONS

Knopf Et Al.: "Metabolic Stimuli To Growth Hormone Release (Protein)" 1968, Excerpta Med, Amsterdam XP000911753 figure 7, p. 612, paragraph 2, p. 613, paragraph 1, p. 617, paragraph 3.

Knopf Et Al..: "Plasma growth hormone response to intravenous administration of amino acids" J. Clinical Endocrinology and Metabolism, vol. 25, 1965, pp. 1140–1144, XP000938527, p. 1140, paragraphs 2, 4, p. 1141, paragraph 3, p. 1144, paragraph 1.

Kuhara Et Al.: "Effects of intravenous infusion of 17 amino acids on the secretion of GH, glucagon and insulin in sheep" American Journal of Physiology, vol. 260, No. 1/1, 1991, pp. e21–e26, XP000938478, p. E21, paragraph 5, p. E22, paragraph 1, table 3, p. E24, paragraph 1, p. E25, paragraph 6.

(Matteini, M., et al. Bollettino–Societa Italiana Biologia Sperimentale. 56(21):2254–60, 1980 Nov. 15).

Drs. Isidori, A., Lo Monaco and Cappa (Isidori, A., et al. Current Medical Research and Opinion 7 # 7 (1981):475–481).

Franco Salomon et al [The New England Journal of Medicine vol. 321 (26) p. 1797–1803) 1989].

J.O.L. Jorgensen et al (Lancet—Jun. 3$^{rd}$, 1989 p. 1221–1225).

Dr. Daniel Rudman published a research paper (Rudman, D., et al. "Effects of Human growth Hormone in men over 60 years Old", New England Journal of Medicine, 323 (1990): 1–6).

Rosen, T., Bengtsson, B.A., Lancet 336 (1990): 285–288.

Alba–Roth, J., Muller, O.A., Schopohl, J. et al. Journal of Clinical Endocrinology and Metabolism 67, #6 (1998): 1186–1189.

Grow Young With hGH by Dr. Ronald Klatz, President of the American Academy of Anti–Aging, published in 1997 by Harper Collins, pp. 30–38, pp. 200–227.

* cited by examiner

Primary Examiner—Thurman K. Page
Assistant Examiner—Charesse L. Evans
(74) Attorney, Agent, or Firm—Anthony C. Edwards

(57) ABSTRACT

A nutritional supplement for ingestion by humans for restoring growth hormone levels consisting of branched chain amino acids chosen from the group leucine, isoleucine, and valine; and free form amino acids chosen from the group lysine, glutamine, ornithine, arginine, and glycine.

5 Claims, No Drawings

SUPPLEMENT FOR RESTORING GROWTH HORMONE LEVELS

CROSS REFERENCE TO RELATED APPLICATION

This application claims priority from U.S. Provisional Patent Application No. 60/131,117 filed Apr. 27, 1999 titled Nutritional Supplement.

FIELD OF THE INVENTION

This invention relates to the field of nutritional supplements, including supplements which elevate release of human growth hormone.

1. Background of the Invention

Until recently human growth hormone (hereinafter alternatively referred to as hGH) was available only in expensive injectable forms and benefits from the restoration of hGH levels available only to those with the ability to pay. Most recently natural substances which can trigger the release of human growth hormone from an individual's own anterior pituitary gland have become available. These are generically referred to as secretagogues. Secretagogues have the ability to restore hGII levels, potentially to the levels found in youth. See for reference the book entitled "Grow Young With hGII" by Dr. Ronald Klatz, President of the American Academy of Anti-Aging, published in 1997 by Harper Collins.

In 1981 a study was published by Drs. Isidori, A., Lo Monico and Cappa (Isidori, A., et al. Current Medical Research and Opinion 7 # 7 (1981):475–481) which demonstrated that a specific combination of amino acids, when ingested orally, would cause an increase in growth hormone levels in humans. If offered a more practical and physiological approach to the previously known fact that intravenous administration of amino acids strongly stimulates the secretion of human growth hormone by the anterior pituitary gland.

Franco Salomon et al [The New England Journal of Medicine Vol. 321 (26) p.1797–1803) 1989] carried out a 6 month randomized, double blind, placebo controlled trial of recombinant human growth hormone on 24 patients suffering from growth hormone deficiency. They noticed an increase in Insulin-like Growth Factor 1 ("IGF-1"), lean body mass and reduction in fat. Metabolic rate was increased and plasma cholesterol lowered.

JO. L. Jorgensen et al (Lancet-Jun. $3^{rd}$, 1989 p. 1221–1225) carried out a 4 month double blind, placebo controlled, crossover study of growth hormone in 22 deficient adults. Muscle thickness increased, fat was reduced. Renal plasma flow and glomerular filtration rates were raised from subnormal levels to levels comparable for their age. IGF-1 levels were also normalized.

In 1990 Dr. Daniel Rudman published a research paper (Rudman, D., et al. "Effects of Human growth Hormone in men over 60 years Old", New England Journal of Medicine, 323 (1990): 1–6) which showed that twelve healthy men aged between 61 and 81, following six months of human growth hormone therapy, had age reversal effects on lean body mass and adipose tissue mass equivalent in magnitude to changes attributable to ten to twenty years of aging. In addition, Dr. Rudman et al noted that alterations in body composition, caused by growth hormone deficiency as we age, can be reversed by replacement doses of hormone in other experiments in rodents, children and adults 20 to 50 years old. Dr. Rudman also noted that "these findings suggest that the atrophy of the lean body mass and its (the body's) component organs and the enlargement of the mass of adipose tissue that are characteristic of the elderly results at least in part from diminished secretion of growth hormone. If so, the age-related changes in body composition should be correctable in part by the administration of human growth hormone, now readily available as a bio-synthetic product".

The primary purpose of hGH is that of stimulating growth, cell repair and regeneration. Once the growth period is over, its primary function becomes that of cell regeneration and repair, helping to regenerate skin, bones, heart, lungs, liver and kidneys to their former youthful cell levels. Elevating hGH levels appears to benefit the immune system. It has also been reported the risk factors for heart attack and stroke may be potentially diminished. Some patients with emphysema have reported that they are less short of breath. Dr. Rudman's study also demonstrated that bone density in the lumbar spine can improve. It has also been shown that wrinkled skin diminishes. Others have reported improvement in presbyopia (the difficulty in focussing due to hardening of the lenses as we age) with some reporting restoration of hair colour and growth. hGH appears to selectively reduce the fat around the abdomen, hips, waist and thighs while at the same time increasing muscle mass. In Dr. Rudman's study, after six months of usage, without exercise, the subjects had an average 8% increase in lean muscle mass and a 14.4% loss of fat.

Dr. Cass Terry and Dr. E. Chein reported on the effects of elevating hGH levels by injection. They showed high frequency-low dose injections of hGII elevated IGF-1 levels. Analyzing the clinical effects of elevating hGH in 202 patients (age 39–74) they showed 75% of the individuals described an increase and improvement in sexual potency as well as frequency of sexual relations, while 62% described improvement in duration of penile erection. Energy levels were improved in 84% of individuals and muscle strength improved in 88%. A 71% increase in healing capacity was noted.

It appears that hGH not only has the ability to restore sexual potency and sexuality in older men, but acts as a mood elevator, restoring a youthful sense of wellness as well as improving sleep. With its potential for affecting cell regeneration and repair, healing of injuries should improve.

hGH, alternatively referred to herein by its medical name Somatotropin, is produced in the anterior pituitary gland situated just below the hypothalamus which is itself situated just below the cerebral cortex of the brain. hGH is one of several hormones secreted by the anterior pituitary gland and, as noted above, influences the growth, regeneration and repair of cells, bones, muscles and organs throughout the body throughout life. Production peaks at adolescence when accelerated growth is occurring and if growing children are deficient in human growth hormone, they remain as pituitary dwarfs. If they have too much they exhibit gigantism (acromegaly).

As is the case with many of our other hormones or their pre-cursors, such as testosterone, oestrogen, progesterone, DHEA and melatonin, hGH levels decline with age. Therapeutically, many of these hormones can be replaced to offset some of the effects of aging such as menopausal symptoms in women or erectile dysfunction in men.

The human body, like every other living entity, works on a daily, or circadian as well as monthly and annual rhythms. Daily growth hormone secretion diminishes with age with roughly half the levels at age forty that we had when we were twenty, and about one-third of those youthful levels at age sixty. In some sixty-year olds the levels are as low as 25% of the hGH levels in a twenty-year old. Symptoms of aging include loss of muscle, increase of fat, decreased physical mobility, decreased energy levels and as a result, diminished socialization, diminished healing ability and an increased risk of cardiovascular disease and decreased life expectancy.

Low hGH levels are associated with the aging process and early onset of disease. For example, Rosen and Bengtsson noted an increased death rate from cardiovascular disease in hGH deficient patients (Rosen, T., Bengtsson, B. A., Lancet 336 (1990): 285–2880). Furthermore, the mechanism of hGH release has been elucidated and is considered to be under the control of Growth Hormone Releasing Hormone (GHRH) and Somatostatin. Somatostatin prevents further release of hGH from the pituitary gland. It has been postulated that one of the key factors in aging is an imbalance in the levels of GHRH and Somatostatin in the combined GHRH/Somatostatin secretion, with an increased action or effectiveness of Somatostatin over GHRH. This leads to an effective reduction in release of the stored hGH from the anterior pituitary gland. Isidori et al have shown the selected amino acids arginine and lysine increase the release of the body's own stored, natural hGH, when taken orally. Matteini showed even low doses of arginine in the region of 200 mg can elevate hGH release. (Matteini, M., et al. Bollettino-Societa Italiana Biologia Sperimentale. 56(21):2254–60, Nov. 15, 1980). It has been suggested one of the mechanisms of action is the inhibitory effect of arginine, and possibly other amino acids, on the secretion and action of Somastostatin (Alba-Roth, J., Muller, O. A., Schopohl, J. et al. Journal of Clinical Endocrinology and Metabolism 67, #6 (1998): 1186–1189).

hGH, once released by the pituitary gland, travels in the circulation and is taken up principally by the liver where it stimulates the production of IGF-1. IGF-1 is then released into the circulation where it attaches to cells in the body and like insulin, triggers the cell to produce certain responses which, with IGF-1, are those of growth, regeneration and repair. Levels of IGF-1 are monitored by the hypothalamus situated just above the pituitary gland. When maximal hGH levels are attained for any individual, these levels trigger the release of Somatostatin. This feedback loop prevents excessive levels of hGH in the body. This feedback loop is extremely efficient at monitoring and maintaining the hGH (and therefore IGF-1) at the optimal level for the individual.

In the prior art, the use of amino acids has essentially been limited to applications where the amino acids have been used as feeding preparations. The amino acids are the final form in which protein is digested from the gastrointestinal tract in mammals. They are essentially pre-digested protein. Given in physiological blends, i.e. those blends that are found occurring naturally in natural proteins such as meat, milk and plants, they can provide the body with the protein nutrients required without the need to pass through the gastrointestinal tract for digestion, i.e. break down to amino acids.

It is thus one object of the present invention to provide a nutritional supplement for elevating hGH release, in particular an amino acid stack, for a synergistic, well tolerated supplemental having the result of increasing or elevating hGH release in those individuals where hGH release rates have slowed as a function of increasing age.

2. Summary of the Invention

The present invention is a nutritional supplement. It is an amino acid stack secretagogue, which, taken orally, stimulates the pituitary gland to produce hGH/Somatotropin. One object of the present invention is to elevate hGH/Somatotropin release. This has the further result of increasing IGF-1 levels. Further objects of the present invention may also result, namely, inhibiting insulin depression; inhibiting hyperglycaemia and increasing insulin effectiveness; enhancing fat conversion, assisting in lowering cholesterol, and normalizing lipid balance.

In summary, the nutritional supplement for restoring growth hormone levels of the present invention comprises in combination, or, alternatively, consists essentially of in combination the following free amino acids (alternatively in the "L" form such as L-Glutamine): lysine, ornithine, glutamine, glycine, leucine, iso-leucine, and valine; and may also include arginine.

In one aspect, the present invention is a nutritional supplement for ingestion by humans for restoring growth hormone levels including or alternatively consisting essentially of:

(a) branched chain amino acids chosen from the group leucine, isoleucine, and valine; and (b) free form amino acids chosen from the group lysine, glutamine, ornithine, arginine, and glycine.

In a further aspect of the present invention, the nutritional supplement for ingestion by humans for restoring growth hormone levels includes or alternatively may consist essentially of all of the amino acids leucine, isoleucine, valine, lysine, glutamine, ornithine and glycine, and may also include arginine.

In a daily dosage the nutritional supplement may include or alternatively consist essentially of:

(a) 1200 mg of L-Lysine;

(b) 1200 mg of L-Arginine;

(c) 798 mg of L-Ornithine;

(d) 498 mg of Glycine;

(e) 240 mg of L-Glutamine;

(f) 420 mg of Leucine;

(g) 420 mg of Iso-Leucine; and (h) 420 mg of Valine.

In alternative formulations, a daily dosage of the nutritional supplement will include, or consist essentially of:

(a) Lysine in the mass range 500 mg and 1500 mg;

(b) Arginine in the mass range 500 mg and 1500 mg;

(c) Ornithine in the mass range 500 mg and 1500 mg;

(d) Glutamine in the mass range 500 mg and 1000 mg;

(e) Glycine in the mass range 400 mg and 1000 mg;

(f) Leucine in the mass range 400 mg and 1000 mg;

(g) Iso-leucine in the mass range 400 mg and 1000 mg; and (h) Valine in the mass range 400 mg and 1000 mg.

DETAILED DESCRIPTION OF PREFERRED EMBODIMENTS

As noted above, elevating hGH levels elevates IGF-1 levels. This can be achieved by secretagogue hGH releasers without the need for injection therapy or oral-hGH forms, or gene manipulation. Secretagogues maintain the body's own natural feedback loop, thus not only releasing hGH naturally but safely. Natural secretagogues may have the ability to more closely mimic the body's youthful hGH secretion patterns than any other hGH therapies currently available. Use of a secretagogue such as the supplement of the present invention has the potential for restoring the body's hGH and IGF-1 levels without interfering with the body's own feedback loop. The supplement of the present invention contains amino acids, formulated as a dietary supplement.

Some amino acids can be made in the body from basic building blocks, but others (nine out of the twenty needed for protein building) are called essential amino acids as the body is unable to manufacture them and they have to be supplied in the food that we eat. Arginine is an amino acid important in creating synthesis. Claims for Arginine include an increase in fat-burning and muscle-building, as well as strengthening the thymus gland by increasing its weight and activity and thereby boosting immunity. There are also claims that Arginine alone will promote healing of burns and wounds as well as enhance male fertility.

Arginine along with Lysine have been demonstrated to cause hGH release when combined in specific proportions. Essential amino acids contained in the supplement of the present invention are Isoleucine, Leucine, Lysine and Valine. Lysine boosts the effectiveness of Arginine and is also said to affect growth as well as having immune-boosting properties of its own. Ornithine can be synthesized in the body and is now also known to help stimulate hGH release. Glutamine can also be synthesized in the body but may not always be made by the body in sufficient quantities in times of stress. Without sufficiently available levels, the gastrointestinal tract does not function as well, and nutrients are less well absorbed. Other amino acids in the supplement of the present invention contribute to the effects of the supplement and the synergy of the amino acids listed above. This type of combination of amino acids is known as an amino acid stack.

The supplement of the present invention works as a dietary supplement by assisting the body's own ability to secrete hGH naturally in a manner which is safe and effective as well as being affordable. When starting the supplement of the present invention it should be taken for a minimum of three months, preferably along with a dietary and exercise regime in order to ensure maximal benefits. Continued usage is suggested for maximum benefit and it is also recommended that it be taken on a six month cycle followed by one month off, or six days per week with one day off, based on our current state of knowledge. The supplement of the present invention may be formulated in a capsule form for ease of ingestion. It should be taken on an empty stomach. This ensures that it is rapidly absorbed into the bloodstream.

What is not taught nor suggested in the prior art, and which the supplement of the present invention provides is the use, in the below disclosed combination and proportions, of amino acids including lysine, glutamine and ornithine, alternatively to also include arginine, to inhibit insulin depression, often seen when hGH levels are elevated. The supplement of the present invention in the specified combination and having the specified quantity of glutamine inhibits hyperglycaemia, while ensuring a natural anabolic muscle building effect by increasing insulin effectiveness. In the supplement of the present invention ornithine is combined with glutamine to enhance fat conversion and assist in lowering cholesterol, while normalizing lipid balance. In the supplement of the present invention, in the specified combination and quantities, amino acids are stacked amino acid secretagogues resulting in balancing glucose, insulin and blood lipids. The supplement of the present invention includes the branched-chain amino acids leucine, isoleucine and valine so as to provide essential nutrients for muscle regeneration and repair. This is of particular importance when a secretagogue is used before exercise.

The combination of types of amino acids, mass ranges and specific formulations have been selected to be synergistically balanced and of adequate quantity to achieve the desired physiological effect, namely, growth hormone release. Improper combinations of the amino acids or insufficient quantities of amino acid salts will be ineffective. The component amino acids are synergistic in the sense that several of them when combined together, arginine, lysine, glutamine, ornithine and glycine, synergistically stimulate the release of human growth hormone. The combination was also chosen to inhibit chemical combination or reaction between the amino acids. Such will not occur because of the crystalline free-form amino acid salts that have been chosen.

A further novel aspect of the supplement of the present invention is the addition of the sulphur-containing branch-chain amino acids leucine, iso-leucine and valine, all of which themselves have a synergistic effect in combination with the human growth hormone that is released in helping to build and improve muscles mass and strength.

With regard to the individual amino acids in particular, ornithine is synergistic with arginine in elevating hGH levels as is lysine synergistic with arginine in elevating hGH levels. Glutamine will elevate hGH levels independently and there is some evidence of a synergistic effect with the three others mentioned above with glycine also producing independent induction of hGH secretion and synergy with the others. The three sulphur-containing branch-chain amino acids, leucine, iso-leucine and valine all have been shown to promote muscle tissue repair and growth particularly in conjunction with human growth hormone as well as increased muscle energy and improvement in skin and wound healing. This in turn would of course help with exercise as vigorous exercise induces a mild level of muscle damage resulting in the aching effect that people notice when they have not been exercising for a while and start to exercise.

Altogether the product is unique in its combination of amino acids in a free-form crystalline state, avoiding an interaction or chain reaction between the amino acids which could result in deterioration and breakdown in the integrity of the product. As well this form avoids the possibility of interaction with the vegetarian gel cap in which the product may be packaged.

In one preferred embodiment, the supplement of the present invention formulation for a one day dose, in 6–8 size 00 capsules, includes the following amino acids in the specified approximate mass ranges:

| LYSINE | 500 mg–1500 mg |
| ORNITHINE | 500 mg–1500 mg |
| GLUTAMINE | 200 mg–1000 mg |
| GLYCINE | 400 mg–1500 mg |
| LEUCINE | 400 mg–1000 mg |
| ISO-LEUCINE | 400 mg–1000 mg |
| VALINE | 400 mg–1000 mg |

Another preferred embodiment may further include:

| ARGININE | 500 mg–1500 mg |

In particular, in one preferred embodiment, the nutritional supplement of the present invention may have the following specific mass composition:

| | |
|---|---|
| L-Lysine | 1500 mg |
| L-Ornithine | 1200 mg |
| Glycine | 498 mg |
| L-Glutamine | 240 mg |
| Leucine | 420 mg |
| Iso-Leucine | 420 mg |
| Valine | 420 mg |

In another specific formulation, the nutritional supplement of the present invention may further include:

| | |
|---|---|
| L-Arginine | 1200 mg | in which case the amount of L-Ornithine may be reduced to 798 mg and the amount of L-Lysine reduced to 1200 mg.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A nutritional supplement for ingestion by humans for restoring growth hormone levels consisting of unmodified rapidly absorbed free-form amino acids, in an amino acid stack which does not include non-amino acid nutritional supplementation, and which, when digested by a user, stimulates release of human growth hormone in the user, said amino acids consisting of:
   (a) branched chain amino acids chosen from the group:
      (i) leucine,
      (ii) isoleucine,
      (iii) valine; and
   (b) free form amino acids chosen from the group:
      (i) lysine,
      (ii) glutamine,
      (iii) ornithine,
      (iv) arginine,
      (v) glycine.

2. A nutritional supplement for ingestion by humans for restoring growth hormone levels consisting of unmodified rapidly absorbed free-form crystalline amino acids, in an amino acid stack which does not include non-amino acid nutritional supplementation, and which, when digested by a user, stimulates release of human growth hormone in the user, wherein said amino acids consist of the amino acids leucine, isoleucine, valine, lysine, glutamine, ornithine and glycine.

3. A nutritional supplement for ingestion by humans for restoring growth hormone levels consisting of unmodified rapidly absorbed free-form amino acids, in an amino acid stack which does not include non-amino acid nutritional supplementation, and which, when digested by a user, stimulates release of human growth hormone in the user, said amino acids consisting of the amino acids leucine, isoleucine, valine, lysine, glutamine, ornithine, glycine and arginine.

4. A nutritional supplement for restoring growth hormone levels, the supplement to be ingested orally by humans in a daily dosage and consisting of unmodified rapidly absorbed free-form crystalline amino acids, in an amino acid stack which does not include non-amino acid nutritional supplementation, and which, when digested by a user, stimulates release of human growth hormone in the user, wherein said amino acids in the daily dosage consist of:
   (a) 1200 mg of L-Lysine
   (b) 1200 mg of L-Arginine
   (c) 798 mg of L-Ornithine
   (d) 498 mg of Glycine
   (e) 240 mg of L-Glutamine
   (f) 420 mg of Leucine
   (g) 420 mg of Iso-Leucine
   (h) 420 mg of Valine.

5. A nutritional supplement for restoring growth hormone levels, the supplement to be ingested orally by humans in a daily dosage consisting of unmodified rapidly absorbed free-form amino acids, in an amino acid stack which does not include non-amino acid nutritional supplementation, and which, when digested by a user, stimulates release of human growth hormone in the user, wherein said amino acids in the daily dosage consist of:
   (a) Lysine in the mass range 500 mg and 1500 mg
   (b) Arginine in the mass range 500 mg and 1500 mg
   (c) Ornithine in the mass range 500 mg and 1000 mg
   (d) Glutamine in the mass range 500 mg and 1000 mg
   (e) Glycine in the mass range 400 mg and 1000 mg
   (f) Leucine in the mass range 400 mg and 1000 mg
   (g) Iso-leucine in the mass range 400 mg and 1000 mg
   (h) Valine in the mass range 400 mg and 1000 mg.

* * * * *